(12) United States Patent
Pappas

(10) Patent No.: US 6,491,726 B2
(45) Date of Patent: Dec. 10, 2002

(54) POSTERIOR STABILIZED PROSTHETIC KNEE REPLACEMENT WITH BEARING TRANSLATION AND DISLOCATION PREVENTION FEATURES

(75) Inventor: Michael J. Pappas, Caldwell, NJ (US)

(73) Assignee: Biomedical Engineering Trust I, NJ (US)

( * ) Notice: Subject to any disclaimer, the term of this patent is extended or adjusted under 35 U.S.C. 154(b) by 0 days.

(21) Appl. No.: 09/796,186

(22) Filed: Feb. 28, 2001

(65) Prior Publication Data

US 2001/0034554 A1 Oct. 25, 2001

Related U.S. Application Data

(60) Provisional application No. 60/187,916, filed on Mar. 8, 2000.

(51) Int. Cl.[7] ................................................. A61F 2/38
(52) U.S. Cl. ........................ 623/20.29; 623/20.27; 623/20.15
(58) Field of Search ..................... 623/20.29, 20.31, 623/20.33, 20.15, 20.27, 20.28, 20.14, 20.21, 20.38

(56) References Cited

U.S. PATENT DOCUMENTS

| | | | | |
|---|---|---|---|---|
| 4,216,549 A | * | 8/1980 | Hillberry et al. | 623/20.29 |
| 4,224,697 A | * | 9/1980 | Murray et al. | 623/20.29 |
| 5,011,496 A | * | 4/1991 | Forte et al. | 623/20 |
| 5,123,928 A | * | 6/1992 | Moser | 623/20 |
| 5,370,701 A | * | 12/1994 | Finn | 623/20 |
| 5,395,401 A | * | 3/1995 | Bahler | 623/20 |
| 5,413,607 A | * | 5/1995 | Engelbrecht et al. | 623/20 |
| 5,879,392 A | * | 3/1999 | McMinn | 623/20 |
| 6,099,570 A | * | 8/2000 | Livet et al. | 623/20.21 |
| 6,117,175 A | * | 9/2000 | Bosredon | 623/20.15 |
| 6,206,926 B1 | * | 3/2001 | Pappas | 623/20.27 |

* cited by examiner

Primary Examiner—Corrine McDermott
Assistant Examiner—Alvin Stewart
(74) Attorney, Agent, or Firm—Anthony J. Casella; Gerald E. Hespos

(57) ABSTRACT

A prosthetic replacement knee joint includes a tibial component, a femoral component, a bearing and a control arm. The tibial component has a superior bearing surface and a conical recess extending into the superior bearing surface. The bearing has an inferior surface slidably engaged with the superior surface of the tibial component and formed with a dovetailed groove therein. The bearing also has a concave superior surface. A notch extends into the posterior extreme of the bearing. The femoral component has a pair of convex arcuate condyles in articular bearing engagement with the superior surface of the bearing. The femoral component also includes a posterior notch having a minor medial-lateral width at the inferior surface of the femoral component and a major width at more superior locations on the femoral component. The control arm has a conical bearing rotatable positioned in the conical recess of the tibial component. The control arm further has a dovetail guide slidably engaged in the dovetail groove of the bearing. A post projects through the notch in the bearing and into the notch of the femoral component. The post has medial and lateral projections that engage portions of the notch in the femoral component that define the major width thereof.

13 Claims, 8 Drawing Sheets

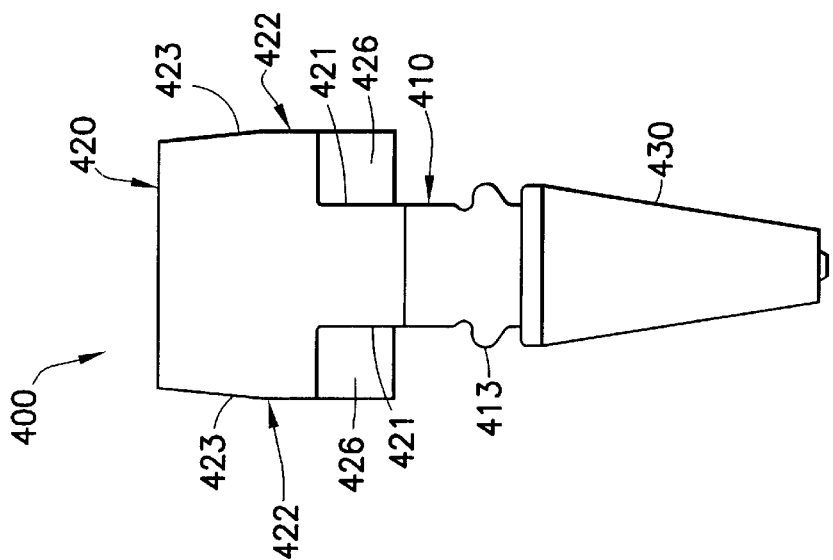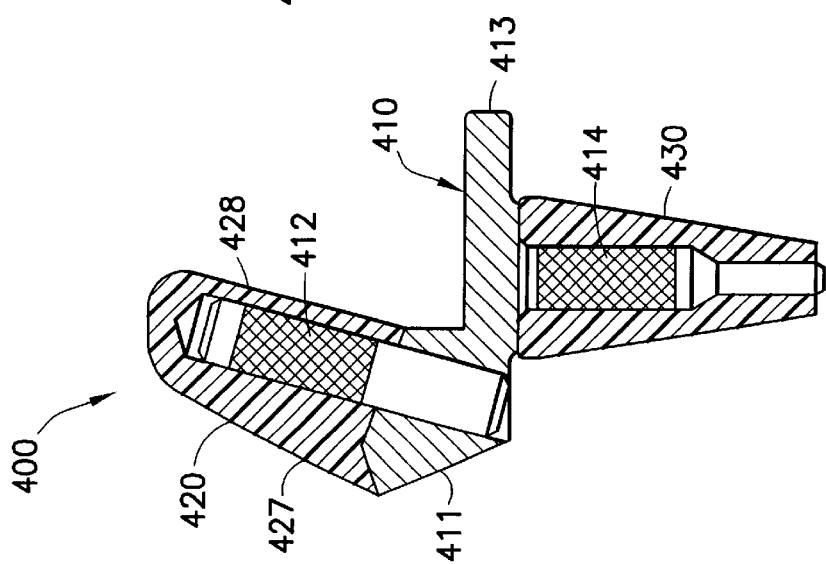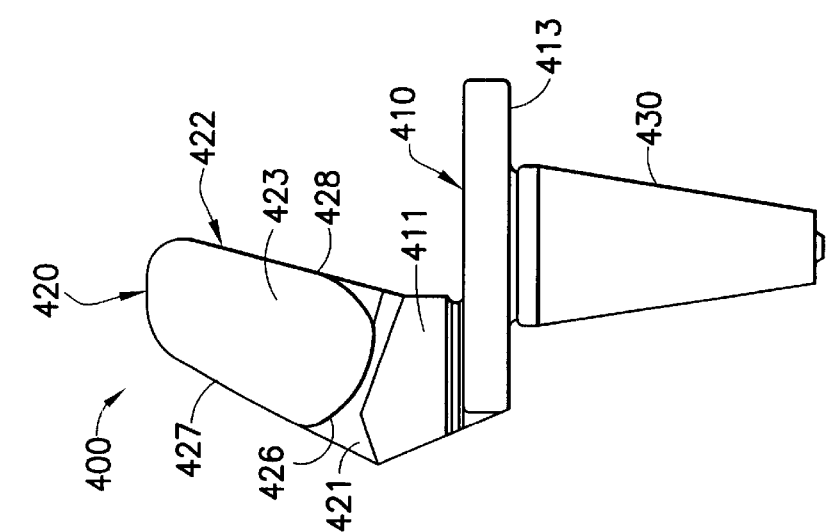

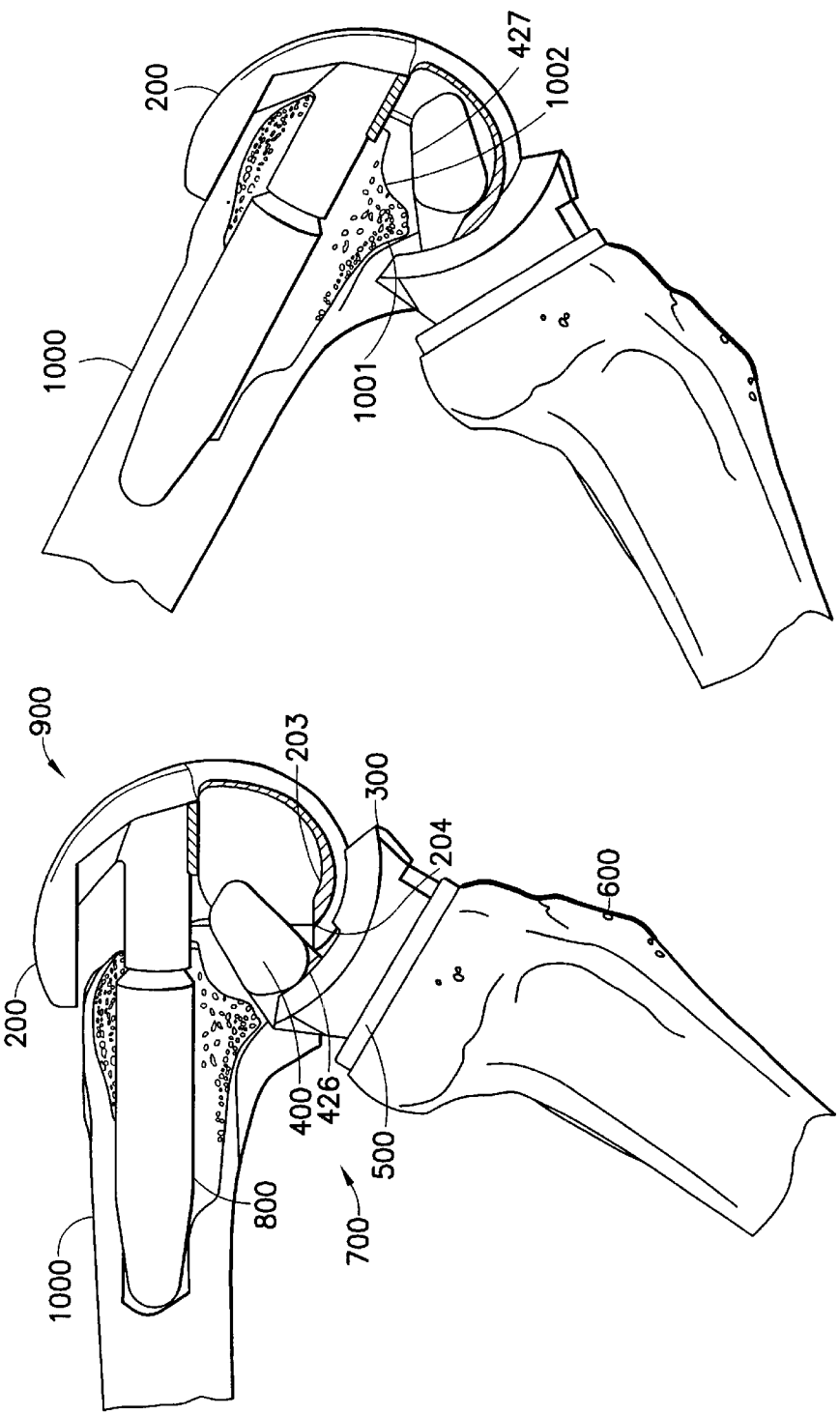

POSTERIOR STABILIZED PROSTHETIC KNEE REPLACEMENT WITH BEARING TRANSLATION AND DISLOCATION PREVENTION FEATURES

This application claims priority on U.S. Provisional Patent Application No. 60/187,916, filed Mar. 8, 2000.

BACKGROUND OF THE INVENTION

1. Field of the Invention

The subject invention relates to a knee joint prosthesis, and particularly a posterior stabilized replacement knee joint prosthesis.

2. Description of the Related Art

A natural knee joint includes the distal end of the femur with articular cartilage, the proximal end of the tibia with articular cartilage and a meniscus between the femur and tibia. The femur and the tibia are held in a proper relationship to the bearing by ligaments. These stabilizing ligaments include the posterior cruciate ligament, the anterior cruciate ligament and collateral ligaments.

Flexion of the knee causes the tibia to rotate relative to the femur about an axis that extends generally in a medial-to-lateral direction and simultaneously causes the contact area of the femur to roll back relative to the tibia. Flexion also generates rotation of the tibia about its own axis. The amount of rotation of the tibia during flexion of the knee is controlled and limited by the ligaments.

The natural knee joint can become damaged or diseased. For example, damage or disease to the knee can deteriorate the articular surfaces of the femur or tibia and can damage the articular cartilage between the bones. The prior art includes prosthetic knee joints to replace a damaged or diseased natural knee. A prosthetic knee joint typically includes a femoral component that is mounted to the distal end of a resected femur, a tibial component mounted to the proximal end of a resected tibia and a bearing between the femoral and tibial components. The inferior face of the femoral component of a prosthetic knee joint typically defines a pair of arcuate convex condyles. The superior face of the bearing has a corresponding pair of arcuately concave regions for articular bearing engagement with the condyles of the femoral component. The superior face of the tibial component may be substantially planar and is disposed in engagement with the inferior face of the bearing.

Prior art prosthetic knee joints have taken many different forms, depending upon the preferences of the orthopedic surgeon, the condition of the natural knee and the health, age and mobility of the patient. Some prior art knee joint prostheses fixedly secure the inferior surface of the bearing to the superior surface of the tibial component. Other prior art knee joint prostheses permit rotational movement between the bearing and the tibial component. Still other prior art knee joint prosthesis permit a controlled amount of anterior-posterior sliding movement between the bearing and a tibial component. Movement of the bearing relative to the tibial component achieves many functional advantages, as described in the prior art. Prior art knee joint prostheses that incorporate certain of the structural and functional features referred to above are disclosed in U.S. Pat. Nos. 4,470,158 and 4,309,778.

As noted above, the inferior bearing surface of the femoral component on most prosthetic knee joints comprises a pair of convexly arcuately condyles. The condyles of the femoral component are in articular bearing engagement with arcuately concave regions on the superior face of the bearing. Thus, the superior face of the bearing typically includes a pair of dished regions each of which has a relatively depressed center portion and a relatively elevated peripheral lip. As explained above, flexion of the knee joint causes the tibia to rotate about a medial-lateral axis relative to the femur. Flexion also causes the tibia to rotate around its own axis. These combined movements may cause the condyles of the femur to ride up or climb the concavities on the superior surface of such a bearing and to approach the peripheral lips of the bearing unless the bearing moves with the femur. Thus, flexion tends to move the relative components of the prosthetic knee toward dislocation. The degree to which dislocation is possible depends on several factors, most significantly, the presence or absence of ligaments and the mobility and configuration of the bearing. The likelihood of dislocation also depends upon the degree of flexion and on the degree of congruency between the inferior articular bearing surface of the femoral component and the superior surface of the bearing. For example, climbing of the femoral component on the bearing is not a significant problem even in fixed bearing knees that have a substantially flat superior surface on the bearing. However, the relatively great incongruency between the inferior bearing surface of the femoral component and the superior surface of the bearing on these prosthetic knees results in a very high contact stress that can damage the bearing. Fixed bearing prosthetic knees that have greater congruency between the femoral component and the bearing provide desirably low contact stress. However, the greater congruency creates the problem of the femoral component climbing on the bearing during flexion or rotation, and hence creates the potential of dislocation.

Valgus-varus stability of a knee joint refers to the ability of the joint to resist the lateral forces or rotary forces that would cause rotation of the tibia relative to the femur in the frontal plane. Lateral forces or rotary movements that cause rotation of the tibia relative to the femur in the frontal plane tend to create a dislocation. Such dislocation is particularly likely to occur on either the medial or lateral side of the prosthesis, depending upon the direction of the lateral forces. Such a dislocation in a prior art prosthesis is shown in FIG. 18 hereto.

The prosthetic knee joint is under a compressive loading during normal activities. As a result, valgus-varus moments typically are resisted adequately by the articulating surfaces of the prosthetic components and by the ligaments. However, there are instances where additional valgus-varus stability may be desired, such as those instances where ligaments are deficient.

Some prior art prosthetic knee joints enhance valgus-varus stability by providing a stabilization post that extends into a posterior region between the femoral condyles. This region would be occupied by the posterior cruciate ligament if that ligament were present. Climbing of the femoral component on the bearing also is a particular problem for prosthetic knee joints that employ a posterior stabilization post. In particular, the climbing of the femoral component on the bearing substantially increases shear forces on the post and can lead to traumatic failure of the prosthesis.

Prosthetic knee joints that permit anterior-posterior sliding movement of the bearing on the tibial component provide superior roll back. In this regard, the term "roll back" refers to a posterior movement of the contact point of the femur relative to the tibia during flexion. Roll back is a potentially desirable feature of a prosthetic knee, as explained below. However, roll back, in prior art prostheses often has caused the femoral component to climb on the bearing, and thus has increased the probability of dislocation.

A prosthetic bearing that can slide posteriorly during flexion reduces impingement between the bearing and anterior soft tissue of the knee. Thus, a prosthetic knee joint with a bearing capable of anterior-posterior sliding movement can reduce discomfort during deep flexion.

A prior art prosthetic knee joint with a stabilizing post and a bearing capable of anterior-posterior sliding movement is shown in U.S. Pat. No. 5,395,401 which issued to Bahler. In particular, U.S. Pat. No. 5,395,401 shows a prosthetic knee having a tibial component and a bearing slidably disposed on the superior face of the tibial component. The inferior surface of the bearing is provided with a dovetailed groove that extends along an anterior-posterior direction at a location between the two concave condyles formed on the superior surface of the bearing. The bearing shown in U.S. Pat. No. 5,395,401 also includes a notch extending into the posterior portion of the bearing at a location between the two concave condyles of the bearing. The notch registers with the dovetailed groove of the bearing. The prosthesis of U.S. Pat. No. 5,395,401 further includes a control arm formed from a metal alloy and having a pin that is pivotally engaged in a recess formed on the tibial component. The control arm includes a dovetailed portion that slidably engages in the dovetailed groove on the inferior surface of the bearing. The control arm shown in U.S. Pat. No. 5,395,401 also has a stabilizing projection that extends through the notch in the bearing and between the condyles of the femoral component. The post is dimensioned for insertion into a box-like structure formed in the femoral component between the two convex condyles of the femoral component. The box-like structure has side walls that engage the stabilizing projection. This would appear to require metal-to-metal sliding contact, which is undesirable. Other embodiments of U.S. Pat. No. 5,395,401 show lateral walls of the bearing that extend into the box-like structure and that lie between the stabilizing projection and the side walls of the box-like structure in the femoral component. This would avoid metal-to-metal sliding contact, but would require a very complex bearing. Nothing in U.S. Pat. No. 5,395,401 would prevent dislocation of the femur from the bearing.

The prior art includes other prosthetic components that have posterior stabilizing posts that extend unitarily from the bearing and into the space between the femoral condyles. Prior art prosthetic joints of this type are shown, for example, in U.S. Pat. Nos. 5,658,342; 5,489,311; 5,330,534; 4,950,298; 4,888,021; 4,634,444 and 4,568,348. All of these prior art prostheses are used for joint replacements where the posterior cruciate ligament cannot be retained or is deficient. Additionally, most of these prior art prosthetic components are for use when both collateral ligaments can be retained.

Despite the various attributes of the prior art prosthetic components, it is desired to provide a prosthetic knee joint that provides superior dislocation resistance than other non-hinged prosthetic knee joints.

It is another object of the subject invention to provide a prosthetic knee joint that avoids any significantly likelihood of dislocation while simultaneously permitting anterior-posterior sliding movement of the bearing relative to the tibial component.

It is a further object of the subject invention to provide a prosthetic knee joint with enhanced dislocation resistance and superior roll back.

Still another object of the subject invention is to provide a prosthetic knee joint that provides enhanced dislocation resistance and reduced shear on a posterior stabilization post.

SUMMARY OF THE INVENTION

A posterior stabilized prosthetic device is provided. The prosthetic device includes a femoral component for mounting to the distal end of a resected femur, a tibial component for mounting to the proximal end of a resected tibia, a bearing disposed between the femoral component and the tibial component and a control arm assembly mounted between at least portions of the bearing and the tibial component.

The bearing of the subject prosthetic joint includes a superior surface having a pair of concave condyles configured for articular bearing engagement with the femoral component as explained further below. The bearing further includes an inferior surface configured for sliding bearing engagement with the superior surface of the tibial component. The inferior surface of the bearing is further characterized by a dovetail grove extending in an anterior-posterior direction. The posterior extreme of the bearing includes a notch or slot centrally disposed between medial and lateral extremes of the bearing and extending continuously from the superior surface to the inferior surface. The notch is substantially aligned with the dovetail groove in the inferior surface of the bearing.

The control arm assembly includes a conical bearing configured for rotary bearing engagement in a conical recess formed in the tibial component. The control arm further includes a dovetailed guide at the superior large diameter end of the conical bearing. The dovetailed guide is dimensioned for sliding movement in the dovetail groove of the bearing and includes opposed anterior and posterior ends that may be spaced from the conical bearing. A post projects superiorly from the posterior end of the dovetailed guide. The post defines a medial-lateral width that permits slidable engagement of the post in the notch of the bearing. Portions of the post spaced from the dovetailed guide include medial and lateral projections. The projections preferably have arcuately convex inferior cam surfaces. The control arm may be formed from a plurality of separate components and from a plurality of different materials. For example, superior portions of the post that have the medial and lateral projections may be formed from plastic. This plastic superior portion of the post may be joined non-rotatably to the remainder of the control arm by a separate metallic support pin that extends upwardly from the dovetailed guide through inferior portions of the post and into the superior portion of the post that has the projections formed thereon. The dovetailed guide preferably is formed from metal and conical bearing preferably has at least outer surfaces formed from plastic. This multi-part construction avoids metal-to-metal or plastic-to-plastic wear.

The femoral component has a superior surface configured for secure mounting to the resected inferior end of the femur. The femoral component further includes an inferior surface defined by a pair of arcuately convex condyles configured for articular bearing engagement with the superior surface of the bearing. A notch or cavity extends into the posterior end of the femoral component. A pair of parallel walls on the femoral component define a width for the notch that is substantially equal to the width of the post of the control arm at portions of the post having the projections thereon. The notch is further characterized by a pair of flanges extending toward one another adjacent the inferior surface of the femoral component. The flanges include a pair of opposed parallel edges that are spaced from one another by a distance slightly greater than the width of the post of the control arm at locations below the projections on the post. The flanges further have concave superior cam that engage the inferior cam surfaces of the post during at least certain ranges of flexion.

The prosthetic device of the subject invention enables the bearing to translate posteriorly in response to flexion and also allows axial rotation of the bearing relative to the tibial component. Additionally, superior portions of the post of the control arm are effectively trapped in the notch or cavity of the femoral component. Consequently, the femoral component cannot be dislocated from the bearing. Still further, the post provides valgus-varus stability that is not present in many prior art knee joint prostheses. Such stability is useful where one or both of the collateral ligaments are compromised.

The posterior translation of the bearing in response to flexion is advantageous since rollback of the femur on the tibia can be accomplished without the femoral component climbing up the posterior articulating surface of the bearing. Such "climb", which would occur with roll back in the prior art prosthetic component, produces additional shearing forces on the post. Climb also increases the compression force on the bearing. However, these problems are avoided with the prosthetic device of the subject invention.

BRIEF DESCRIPTION OF THE DRAWINGS

FIG. 6 is a side elevational view of the control arm.

FIG. 7 is a cross-sectional view of the control arm.

FIG. 8 is a rear elevational view of the control arm.

FIG. 11 is a side elevational view of the prosthetic component during implantation of the femoral component into the knee.

FIG. 12 is a cross-sectional view similar to FIG. 11, but showing the knee at a more advanced stage of implantation.

DETAILED DESCRIPTION OF THE PREFERRED EMBODIMENT

Figure 2:
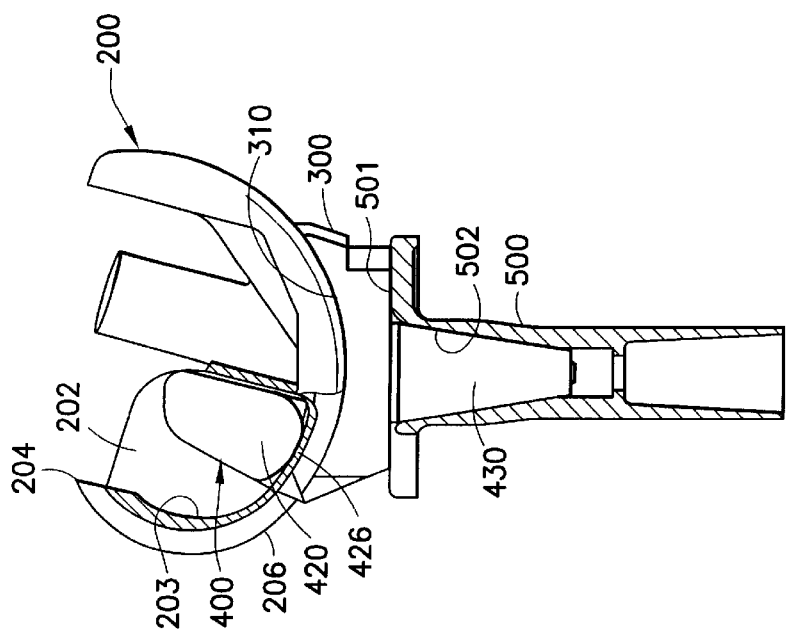
FIG. 2 is a cross-sectional view of the prosthetic device shown in FIG. 1.
Figure 1:
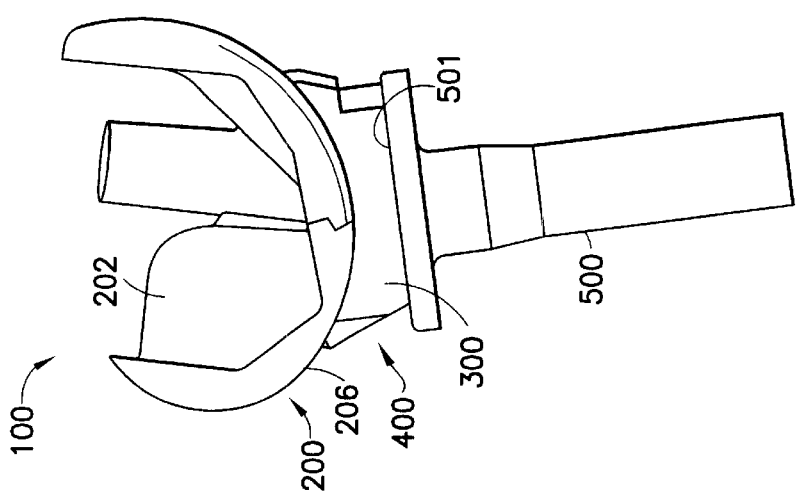
FIG. 1 is a side elevational view of a prosthetic device in accordance with the subject invention.

The dislocation resistant posterior stabilized knee replacement 100 consists of a femoral component 200, a bearing 300, a control arm assembly 400 and a tibial platform 500 as shown in FIGS. 1 and 2.

Figure 3:
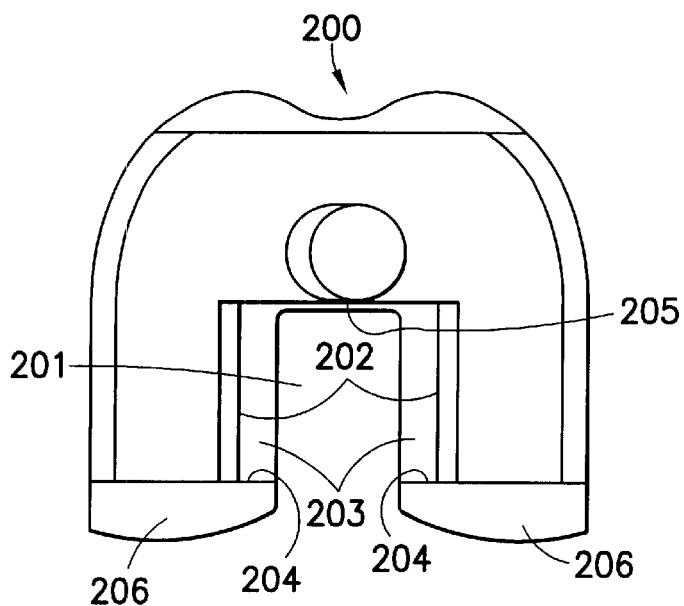
FIG. 3 is a top elevational view of the femoral component.

The femoral component 200, as shown in FIG. 3, contains a posterior notch or cavity 201 with medial and lateral cavity sidewalls 202. Concave femoral cam surfaces 203 face superiorly on flanges that project toward one another from the respective medial and lateral cavity sidewalls 202. The flanges extend posteriorly and superiorly to edges 204 that are in an extreme superior position in a full extension position of the prosthesis as shown in FIGS. 1 and 2. The notch 201 is further defined by an anterior wall 205 that extends between the medial and lateral sidewalls 202. The femoral component 200 is further defined by inferior convex condyles 206 that are disposed in articular bearing engagement with the bearing 300 as explained further below. FIG. 2 shows a lateral view of the femoral component 200 with the one posterior femoral condyle 206 broken away so as to show details of the posterior notch 201.

Figure 4:
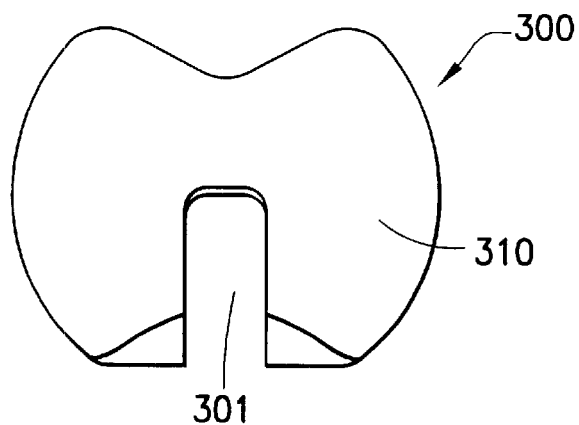
FIG. 4 is a top elevational view of the bearing.
Figure 5:
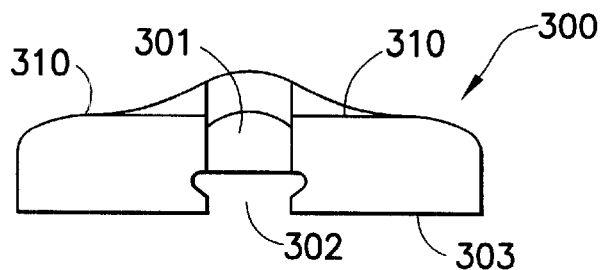
FIG. 5 is a rear elevational view of the bearing.

The bearing 300, as shown in FIGS. 4 and 5, contains a posterior notch or slot 301 and a dovetail guide slot 302. The dovetail guide slot 302 is formed into an otherwise substantially planar inferior surface 303 and extends anteriorly from the posterior notch 301. The bearing 300 also includes medial and lateral concave articular bearing surfaces 310 which are configured for articular bearing engagement with the condyles 206 of the femoral component 200.

The control arm assembly 400, as shown in FIGS. 6–8, comprises a control arm 410, a post 420 and a conical bearing 430. The control arm 410 comprises a post support 411, a post support pin 412, a dovetail guide 413 and a conical bearing support 414, all of which are formed from metal. The dovetail guide 413 has a dovetail cross-sectional shape that is configured for sliding reception in dovetail guide slot 302 in bearing 300. The post support 411 is formed unitarily with the posterior end of the dovetail guide 413 and is dimensioned to extend into the posterior notch 301 in the bearing 300. The post support pin 412 may be formed separately from both the post support 411 and the dovetail guide 413 and projects superiorly from the post support 411, as shown most clearly in FIG. 7. The exterior surface of the post support pin 412 may be knurled to achieve a secure force fit mounting of the post 420 thereon as explained further below. The conical bearing support 414 projects inferiorly from the dovetail guide 413 and also includes a knurled exterior surface.

The post 420 is formed from plastic and is mounted to the post support pin 412. Inferior portions of the post 420 define medial and lateral surfaces 421 that align respectively with medial and lateral surfaces of the post support 411. Superior portions of the post 420 are characterized by medial and lateral projections 422 that project in medial and lateral directions outwardly from the inferior medial and lateral surfaces 421. The medial and lateral projections 422 have side surfaces 423 that taper slightly toward one another at more superior positions on post 420. The medial and lateral projections 422 further define inferior convex post cam surfaces 426 that will engage the femoral cam surfaces 203 as explained further below. The inferior post cam surfaces 426 extend through an arc from a posterior post surface 427 to an anterior post surface 428.

Conical bearing 430 of the control arm assembly 400 is unitarily formed from a plastic material and is force fit onto the knurled outer surface of the conical bearing support 414.

The tibial platform 500 has a substantially planar superior bearing surface 501 and a conical hole 502 into which the conical bearing 430 of the control arm assembly 400 is placed on implantation.

The femoral component 200 is similar to that described in U.S. Pat. No. 5,702,466 except for the addition of the posterior cavity or notch 201 detail and a modular post for accepting an extension providing enhanced fixation. The bearing 300 is similar to that described in U.S. Pat. No. 5,824,096 on the hinge knee except for the posterior slot 301 which now breaks through the posterior wall of the bearing 300 and the addition of a dovetailed guide slot 302. The tibial platform 500 can be the same as that described in U.S. Pat. No. 5,702,466. The embodiment shown here is a version used where an extension is added to the distal end of the platform 500 to enhance fixation where needed.

Figure 10:
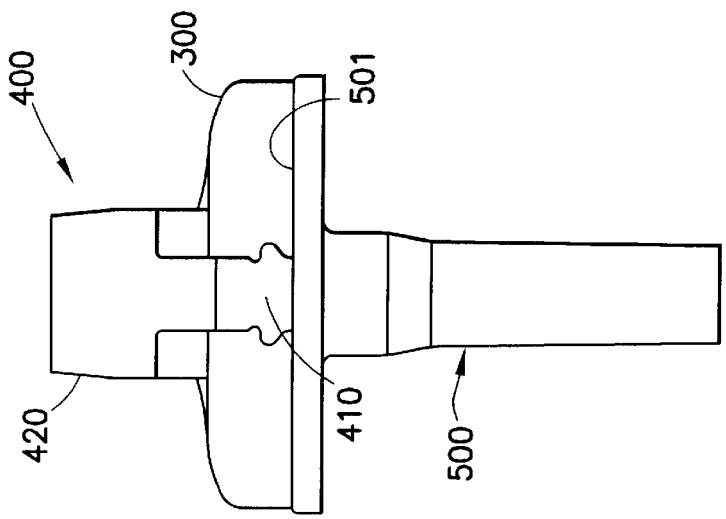
FIG. 10 is a rear elevational view of the tibial component, the bearing and the control arm.
Figure 9:
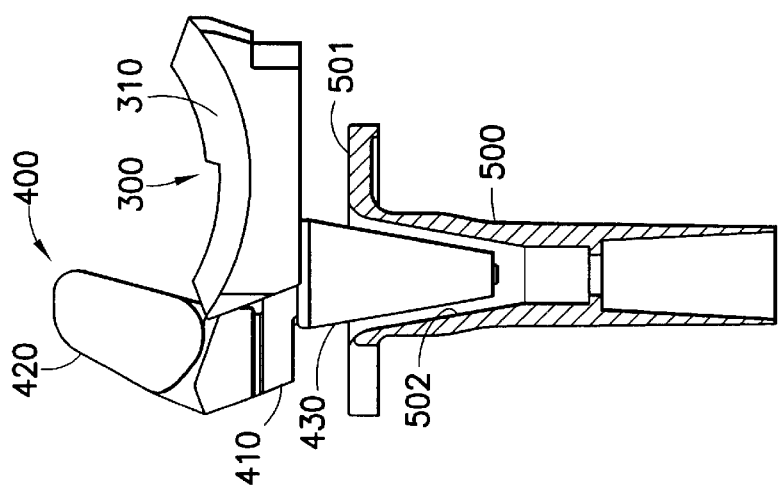
FIG. 9 is an exploded cross-sectional view of the tibial component, the bearing and the control arm.

FIGS. 9 and 10 illustrate the assembly of the bearing 300 onto the control arm assembly 400 and into the tibial platform 500.

The femoral component 200, the control arm 410 and tibial platform 500 are preferably made of titanium alloy coated with a TiN coating disclosed in U.S. Pat. No. 5,702,448 and marketed by Endotec Inc. under the trademark UltraCoat®. The bearing 300, post 420 and conical bearing 430 preferably are made of UHMWPe.

Implantation is illustrated in FIG. 11. The tibial platform 500 is implanted into the tibia 600 in the usual fashion and the bearing 300 with the control arm assembly 400 pre-assembled are mounted onto the tibial platform 500 as shown in FIGS. 9 and 10. The knee 700 is flexed to about 120° and the femoral component assembly 900 consisting of the femoral component 200 with an attached extension 800 is inserted onto the femur 1000. As the femoral component assembly 900 is moved proximally, the superior edges 204 of the femoral cam surfaces 203 clear the inferior post cam surfaces 426 and allow full seating of the femoral component assembly 900 onto the femur 1000 as shown in FIG. 12. The posterior distal region 1001 of the femur 1000 must have a relief 1002, as shown in FIG. 12, to clear the posterior post surface 427 and to provide the full flexion needed to implant the femoral component assembly 900.

Figure 14:
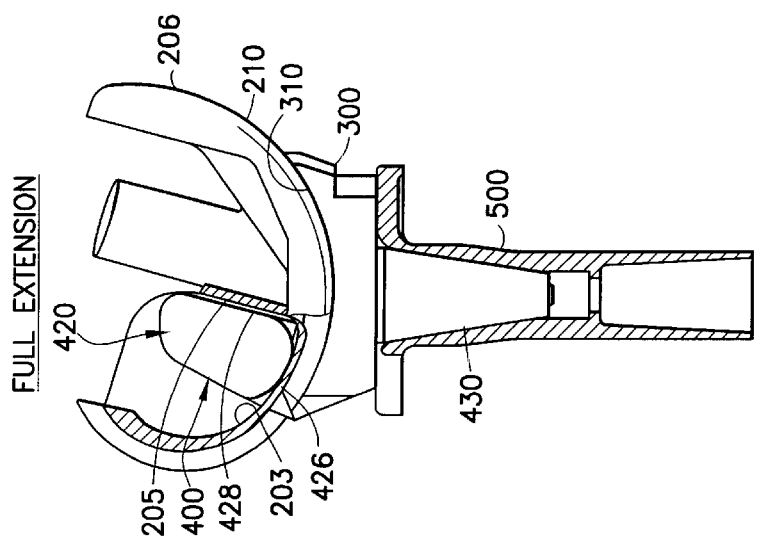
FIG. 14 is a cross-sectional view of the assembled prosthetic device at full extension.

As illustrated in FIG. 12 the tibia 600 cannot be dislocated posteriorly since the presence of the posterior distal region 1001 inhibits posterior tibial motion by impingement with the posterior post surface 427. As shown in FIG. 14, the anterior wall 205 of the posterior notch 201 in the femoral component 200 and the anterior cam surfaces 428 of the post 420 prevent anterior dislocation of the tibia 600. The side surfaces 423 of the medial and lateral projections 422 of the post 420 engage the sidewalls 202 in the posterior cavity 201 of the femoral component 200, thereby preventing medial-lateral dislocation. Thus, the control arm assembly 400 is trapped in the femoral component 200 and cannot be dislocated from it.

Figure 13:
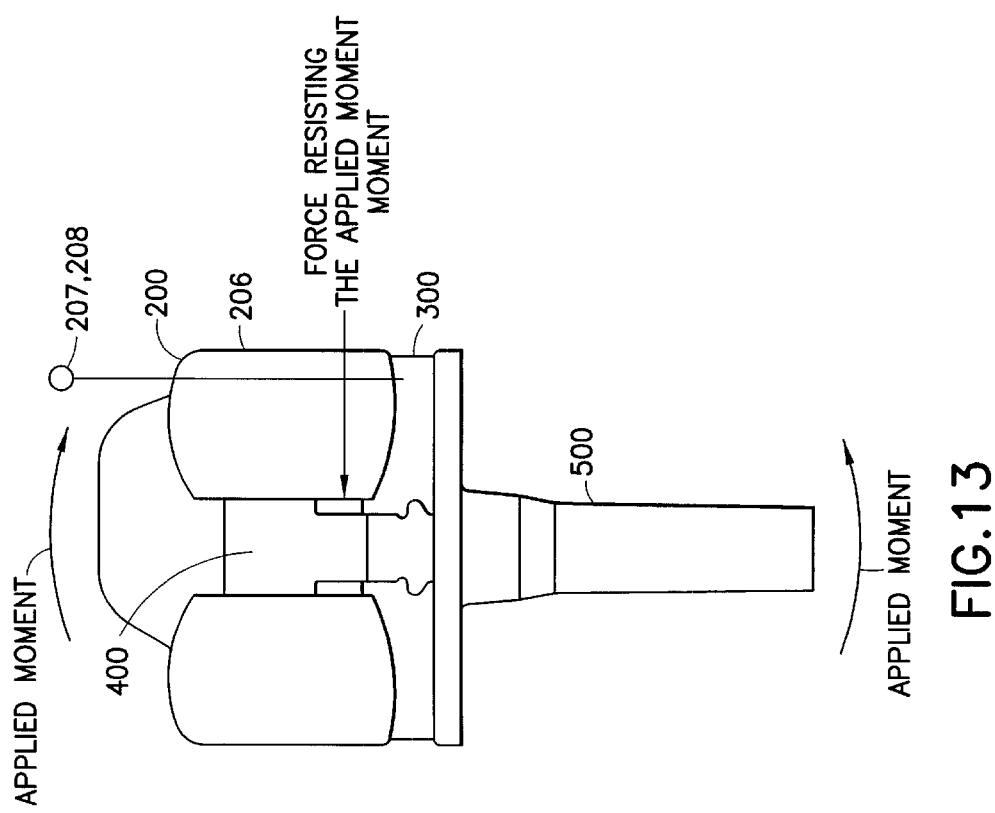
FIG. 13 is a schematic rear elevational view of the assembled prosthetic device showing different forces applied to the prosthetic device.

There are two means of valgus-varus stability. Under load bearing conditions the normal compressive load will press the femoral condyles 206 against the matching articular bearing surface 310 of the bearing 300. The match is such that under compression any rotation of the femoral component 200, in the plane of FIG. 13 must occur around an axis 207 through the center of curvature 208 of the femoral condyle 206. Rotation about axis 207 produces impingement between the outer side surfaces 423 of the medial and lateral projections 422 on the post 420 and the sidewalls 202 of the posterior notch 201 in the femoral component 200. This contact produces a reaction force resisting any valgus-varus moment applied to the joint. Thus bending of the post 420 and post support pin 412 need not occur to resist the applied moment. The side surfaces 423 of the medial and lateral projections 422, as shown in FIG. 8, are tapered slightly to prevent such bending during load bearing.

During non-load bearing phases where any valgus-varus moment is quite small, the post 420 may be subject to small bending loads since joint compression may not occur. The post 420 support pin 412 must be strong enough in bending to resist such moments.

Figure 17:
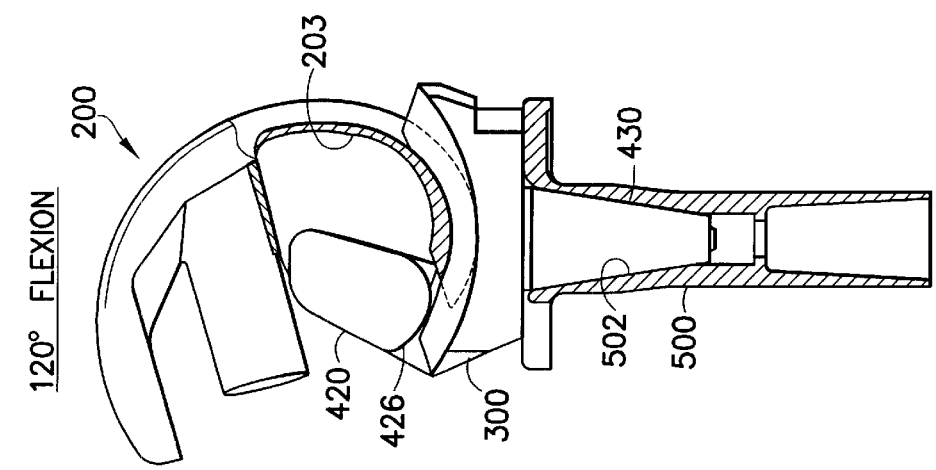
FIG. 17 is a cross-sectional view similar to FIGS. 14–16, but showing the prosthetic device at 120° flexion.
Figure 16:
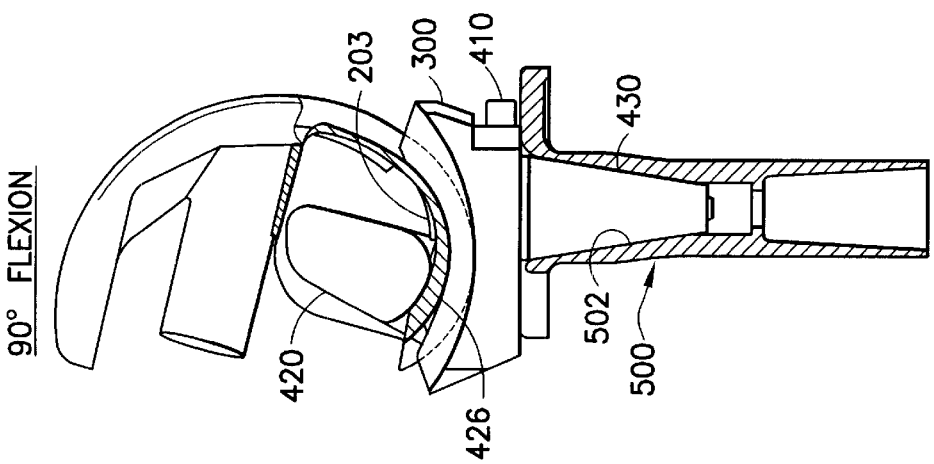
FIG. 16 is a cross-sectional view similar to FIGS. 14 and 15, but showing the prosthetic device at 90° flexion.
Figure 15:
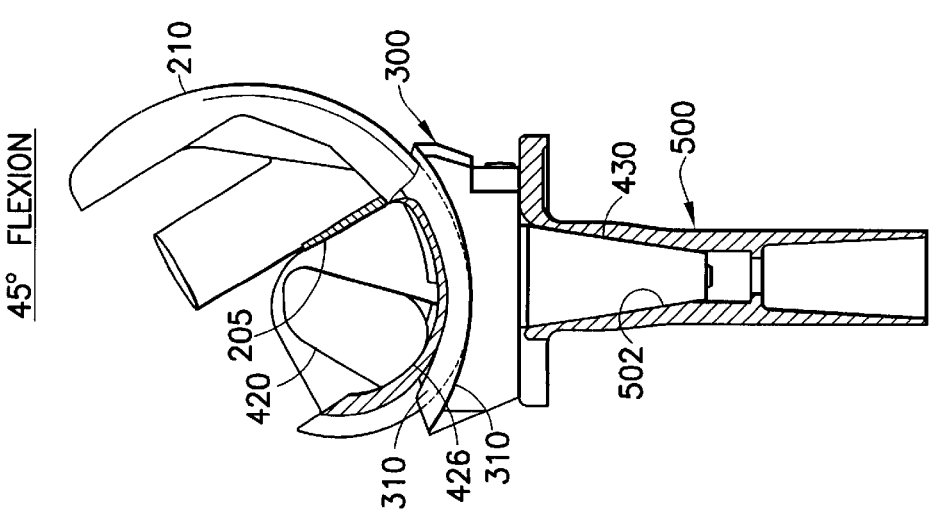
FIG. 15 is a cross-sectional view similar to FIG. 14, but showing a prosthetic device at 45° flexion.
Figure 18:
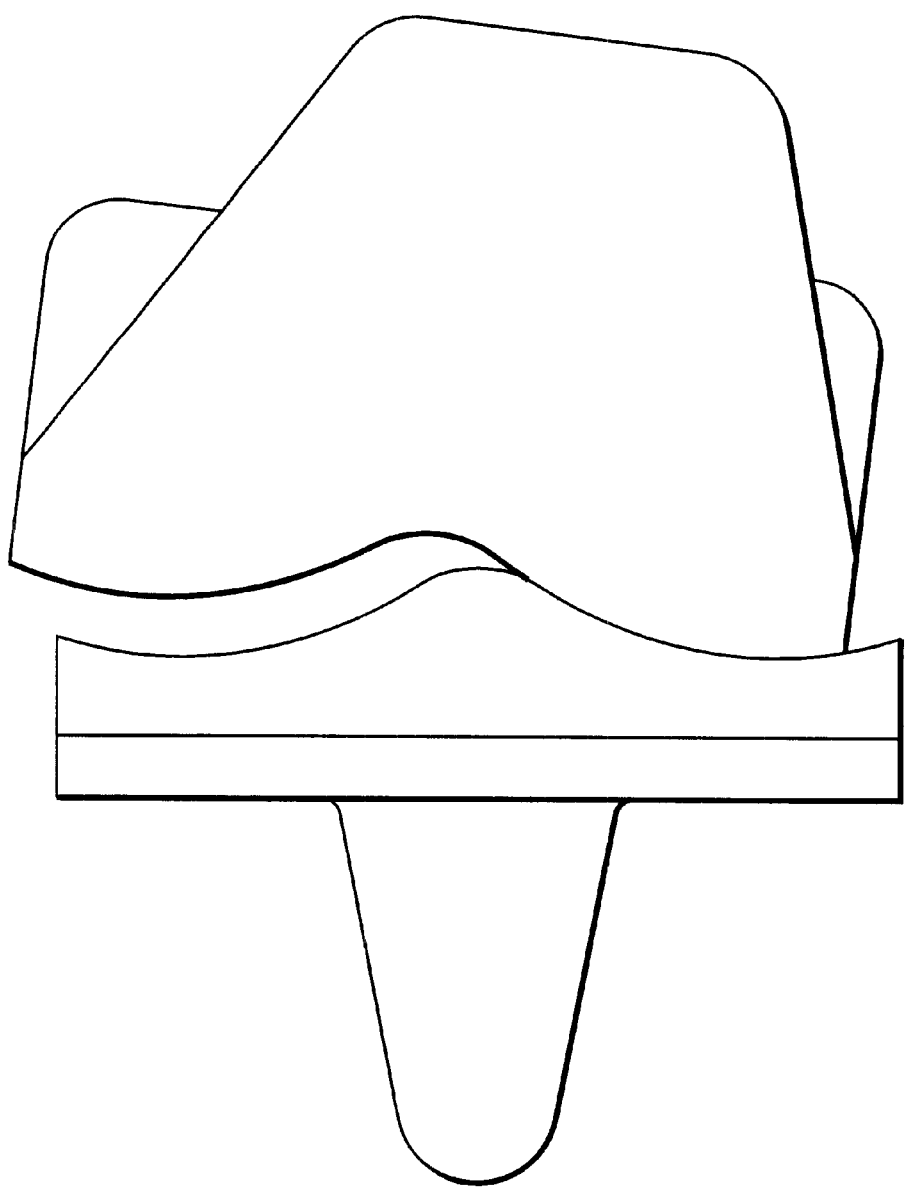
FIG. 18 is a rear elevational view of a prior art prosthetic joint showing partial dislocation.

The cooperative action of the cavity cam surfaces 203 and post cam surfaces 426 are illustrated in FIGS. 14–17. In full extension, as shown in FIG. 14, the cam surfaces 203, 426 need not be in contact. They act only to prevent A-P dislocation in the absence of load bearing. Under load bearing the shape of the femoral articular surface 210 of the femoral condyles 206 pressing against the tibial articular surface 310 provides stability and position. As flexion progresses, as shown in FIGS. 15 and 16, the concave superior femoral cam surfaces 203 will engage the convex inferior post cam surfaces 426 and force the femoral component 200 posteriorly. The compressive force on the bearing 300 and the concave shape of the articular bearing surfaces 310 will cause the bearing 300 to move with the femoral component 200. This posterior movement, or femoral rollback, improves quadriceps effectiveness as is well known. This rollback is present for any normal load bearing activity likely to be performed by a knee replacement patient requiring a posterior stabilized device. This posterior movement may be lost at full flexion, as shown in FIG. 17, but this is unimportant since load bearing does not normally occur in this motion phase, or occurs very infrequently. Furthermore, since the posterior wall of the bearing 300 may come into contact with the femur 1000 during deep flexion it is desirable to allow the bearing 300 to move anteriorly on the tibial component 500 thereby allowing greater flexion.

This prosthesis is novel in that it is non-dislocating and it does not produce significant bending of the post from an applied valgus-varus moment during compressive load bearing. Additionally the prosthesis makes use the medial edges of the femoral condyles 206 as cams 203 and inferior surfaces 426 of projections 422 on the post 420 to produce femoral rollback and posterior stability. A mobile bearing posterior stabilized knee where primarily the bearing is under compressive load provides A-P stability. Further, the bearing 300 moves with the femoral component 200 during rollback thereby eliminating "climb" and thus maintaining best contact between the femoral and bearing articulating surfaces 206 and 310, and reducing shear forces on the post 420.

What is claimed is:

1. A dislocation resistant knee joint prosthesis comprising:

a femoral component having an inferior articular bearing surface with medial and lateral convex condyles, a posterior notch extending anteriorly into a posterior face of the femoral component, said notch being defined by medial and lateral cavity sidewalls and an anterior wall extending between said medial and lateral cavity sidewalls, with parallel medial and lateral flanges extending from said medial and lateral cavity sidewalls adjacent the inferior articular bearing surface of the femoral component;

a tibial component;

a bearing disposed between the femoral and tibial components, the bearing having a concave superior bearing face in articular bearing engagement with the inferior articular bearing surface of the femoral component, the concave superior bearing face being configured for noncongruent bearing engagement with the convex condyles during selected ranges of flexion of the knee joint prosthesis, the bearing further having an inferior bearing face in sliding and rotational bearing engagement with the tibial component, a posterior notch extending anteriorly into a posterior face of the bearing and a groove formed in the inferior bearing face of the bearing and extending anteriorly from the posterior notch in the bearing; and a control arm assembly comprising a control arm slidably engaged in the groove of the bearing, the control arm being pivotally mounted on the tibial component, a post extending in a superior direction from the control arm through the posterior notches of the bearing and the femoral component, the post having medial and lateral cam projections which slidably engage said medial and lateral cavity sidewalls of the femoral component for enhancing valgus-varus stability of the knee joint prosthesis, said medial and lateral cam projections engaging superior surfaces of the flanges of the femoral component for generating posterior translation of the bearing during flexion of the knee joint prosthesis and preventing dislocation.

2. The knee joint prosthesis of claim 1, wherein said flanges of said femoral component having inferior surfaces substantially conforming to shapes defined by said convex condyles, said superior surfaces of the flanges being arcuately concave.

3. The knee joint prosthesis of claim 2, wherein the medial and lateral cam projections of the post have arcuately convex inferior cam surfaces for bearing engagement against the arcuately concave superior surfaces of the flanges of the femoral component.

4. The knee joint prosthesis of claim 1, wherein the tibial component has a superior bearing surface with a recess, the control arm assembly comprising a projection pivotally engaged in the recess of the tibial component for achieving the pivotal mounting of the control arm assembly on the tibial component.

5. The knee joint prosthesis of claim 4, wherein the recess in the tibial component and the projection of the control arm assembly have complimentary conical shapes.

6. The knee joint prosthesis of claim 4, wherein the superior bearing surface of the tibial component is substantially planar, and wherein the inferior bearing face of the bearing is substantially planar.

7. The knee joint prosthesis of claim 1, wherein the groove in the inferior face of the bearing is a dovetail groove, and wherein the control arm has a dovetail configuration for slidable engagement in the groove of the bearing.

8. The knee joint prosthesis of claim 1, wherein the femoral component, the tibial component and the control arm are formed from metal, and wherein the bearing and the post are formed from plastic.

9. The knee joint prosthesis of claim 8, wherein the control arm assembly comprises a metallic post support pin extending from said control arm and into said plastic post, said metallic post support pin resisting shear forces generated on said post during flexion of said knee joint prosthesis.

10. The knee joint prosthesis of claim 1, wherein the flanges of the femoral component are substantially equally spaced from one another at all locations along said notch.

11. The knee joint prosthesis of claim 1, wherein the bearing is unitarily formed from a UHMWPe.

12. The knee joint prosthesis of claim 1, wherein the femoral component and the tibial component both are formed from metallic materials.

13. A dislocation resistant knee joint prosthesis comprising:

a tibial component having a superior bearing surface with a recess therein;

a control arm having an inferior projection rotatably engaged in the recess of the tibial component, a post extending superiorly from the control arm, the post having medial and lateral projections with convex inferior cam surfaces;

a bearing having an inferior surface in sliding bearing engagement with the superior bearing surface of the tibial component, a posterior notch extending anteriorly into a posterior face of the bearing, portions of said post of said control arm inferiorly of the medial and lateral projections being slidably engaged in said posterior notch of said bearing, said bearing further having a groove in the inferior bearing face and extending anteriorly from said notch, the control arm being slidably engaged in the groove; and a femoral component having an inferior articular bearing surface with medial and lateral convex condyles in articular, noncongruent bearing engagement with the superior bearing face of the bearing, a posterior notch extending anteriorly into a posterior face of the femoral component, said posterior notch being defined by medial and lateral flanges adjacent the inferior articular bearing surface of the femoral component, said flanges having concave superior bearing surfaces engaged with the convex inferior cam surfaces of the projections on the post for generating roll back of the femoral component during flexion of the knee joint prosthesis and preventing dislocation of said femoral component.

* * * * *